United States Patent [19]

Morgan et al.

[11] Patent Number: 5,020,538
[45] Date of Patent: Jun. 4, 1991

[54] LOW NOISE MAGNETOENCEPHALOGRAM SYSTEM AND METHOD

[75] Inventors: Nelson H. Morgan, Berkeley; Alan S. Gevins, San Francisco, both of Calif.

[73] Assignee: SAM Technology, Inc., San Francisco, Calif.

[21] Appl. No.: 435,754

[22] Filed: Nov. 14, 1989

Related U.S. Application Data

[63] Continuation-in-part of Ser. No. 231,385, Aug. 12, 1988, abandoned, and a continuation-in-part of Ser. No. 27,264, Mar. 18, 1987, abandoned.

[51] Int. Cl.$^5$ .............................................. A61B 5/05
[52] U.S. Cl. ................................ 128/653 R; 128/901; 324/248; 324/260
[58] Field of Search ................... 128/653 R, 731, 901; 324/244, 248, 260

[56] References Cited

U.S. PATENT DOCUMENTS

| | | | |
|---|---|---|---|
| 3,697,870 | 10/1972 | Brenner | 324/244 |
| 3,980,076 | 9/1976 | Wikswo, Jr. et al. | 128/653 R |
| 4,324,255 | 4/1982 | Barach et al. | 128/653 R |
| 4,386,318 | 5/1983 | Burbank et al. | 324/244 |
| 4,389,612 | 6/1983 | Simmonds et al. | 324/248 |
| 4,613,817 | 9/1986 | Hoenig | 324/248 |
| 4,675,606 | 6/1987 | Ganguly | 324/244 |

Primary Examiner—Ruth S. Smith
Attorney, Agent, or Firm—Eliot S. Gerber

[57] ABSTRACT

A magnetoencaphalogram (MEG) detects the neuromagnetic brain signals of a subject by bringing a set of magnetic sensors, preferably SQUIDs (superconducting quantum interference device), close to the scalp of the subject. The adverse effect of environmental magnetic noise is reduced by using a second set of magnetic sensors which are placed near the subject. The system includes a bandpass filter, to divide the signals from the various sensors into predetermined frequency bands, and a computer to provide a least squares noise component estimate of the noise from each brain wave sensor and to calculate therefrom a filtered brain wave signal having reduced noise.

10 Claims, 5 Drawing Sheets

LOW NOISE MAGNETOENCEPHALOGRAM SYSTEM AND METHOD

This application is a continuation-in-part application based upon application Ser. No. 07/231,385, filed Aug. 12, 1988, now abandoned, and Ser. No. 027,264, filed Mar. 18, 1987, now abandoned.

BACKGROUND OF THE INVENTION

1. Field of the Invention

The present invention relates to medical instruments and more particularly to a low noise magnetoencephalogram (MEG) system.

2. Description of the Related Art

The human brain produces both electrical and magnetic signals. It is conventional to detect both ongoing spontaneous electrical brain activity and evoked electrical brain activity (EP) by non-invasive electrodes connected to the scalp of the patient using an electroencephalograph (EEG). For example, evoked brain activity (EP) may be stimulated by an external stimulus such as a flashed light.

The weak magnetic fields at the scalp, produced by the flow of electrical current within the brain, may be detected by a non-invasive magnetoencephalogram (MEG) whose detecting coils are positioned close to the scalp. There are indications, for example, that the magnetoencephalogram may be used to locate the origin of seizures within the human brain. The earliest MEG devices were constructed inside a magnetically shielded room, since the magnetic fields sought to be detected are much weaker than environmental fields. The environmental field, which is "noise" in the system, changes character over time. Even when the magnetic detecting instrument is brought up close to the patient's scalp, the brain's magnetic signals are so faint that they may be drowned out, even after compensating for the earth's magnetic field, by the stronger magnetic field of a truck passing by outside the building. Unfortunately, a properly magnetically shielded room is expensive. The room must be large enough for the patient, the operators and the sensitive equipment and may cost over two hundred thousand dollars.

An alternative to the use of a magnetic shielded room is to improve the signal sensitivity and noise suppression of the magnetic field detector. The preferred type of MEG uses a "SQUID" (superconducting (S) quantum (QU) interference (I) device (D)). The SQUID operates at cryogenic temperature at which metal loses its electrical resistivity. In one type of SQUID a metal film is deposited on a cylindrical quartz cylinder having a narrow bridge "weak link". A magnetic field will increase the energy, making the superconducitng state unstable so that the weak link converts to its normal state (non-superconducting), allowing one flux quantum to enter. The conduction of the ring is monitored by a radio frequency circuit whose sensitivity is increased with a feedback current circuit. Generally a "flux transporter" is used in which a primary coil ("detection coil"), of superconductive wire, is connected to a secondary coil ("input coil") contained in the superconducting chamber with the SQUID. For example, the chamber is a "dewar" vacuum chamber filled with liquid helium. For example, five primary coils are placed closely about the patient's head to detect the brain's magnetic fluxes. Those fluxes create responses in the detection coils which are communicated to the SQUIDS, which produces a voltage proportional to the net magnetic flux on each detection coil. The flux transporter and the SQUID constitute a "magnetometer". When used to detect brain activity, the system is called a "magnetoencephalograph" or "MEG".

It has been suggested that a MEG system may be used in a magnetically unshielded room by forming the detection coil with oppositely directed loops (a "gradiometer"), so that external magnetic flux will be detected in both loops and their effects will be canceled. The loops may be arranged, for relative insensitivity to spacially uniform fields and gradients, in a "second derivative gradiometer".

However, the brain's spontaneous neuromagnetic activity is weak ($10^{-12}$ Tesla) and the neurpmagnetic evoked response is even weaker ($10^{-13}$ Tesla). Consequently, it is difficult to detect such activity in the presence of external magnetic fields which produce noise in the system. It has been suggested that the signal/noise ratio may be improved by using an averaging computer which passes signals which are in synchronism with the stimulus. Since the noise is random, the cumulative average should represent the signals as the random noise cancels itself out. Improvements of signal/noise ratio of 10:1 have been reported. However, that technique is applicable only to evoked response (EP) and not to spontaneous brain activity.

Efficient and effective noise cancellation is critical to the development of the magnetoencephalogram (MEG) as a clinical tool. This noise contamination from environmental magnetic fields is a major factor, even in the latest generation, multichannel, second-order gradiometer of DC SQUID (superconducting quantum interference device) systems. For example, for the Biomagnetic Technology Inc. Model 607 magnetometer, removal of this environmental magnetic field contamination requires using the information from four SQUIDS (which act as environmental noise reference sensors) to filter the corresponding noise out of the seven channels which sense both bonafide brain signals and environmental noise. The channels used only to detect environmental noise will be called the noise reference signals or channels, and the channels which detect both neuromagnetic brain signals and environmental noise will be called the brain signals or channels. The noise reference channels monitor the three orthogonal components of the ambient (environmental) magnetic field and, usually, the gradient of the field along the axis of the dewar. In the current commercial systems, these noise reference signals are scaled through a manual procedure which involves static setting of eight independent parameters, four for the noise amplitude and four for the time derivatives of the noise, for each of the seven brain signal channels. This is a total of 56 manual adjustments. Such manual adjustments necessarily are suboptimal and cannot compensate for rapid variations in the relationship between the noise reference and brain signal channels, for example, due to changes in the environment or movement of the dewar from one position to another.

The book, H. Weinberg et al, BIOMAGNETISM: APPLICATIONS AND THEORY (Pergamon Press 1985) contains a chapter, Williamson et al, FIVE CHANNEL SQUID INSTALLATION FOR UNSHIELDED NEUROMAGNETIC MEASUREMENTS (pgs. 46-51, incorporated by reference herein). In Williamson nine SQUIDS are used in an unshielded environment. Five SQUIDS, having second order gradiometers, monitor brain activity (5-channel magnetometer) and four SQUIDS monitor three components of the ambient field and one component of the gradient. The four SQUIDS attempt to cancel background (environmental) noise by an analog noise cancellation system requiring 40 static adjustments for the 5 brain signal channel magnetometer. The results from this cumbersome procedure are that MEG recordings are often unusable because of overwhelming residual contamination by environmental noise sources. In practice, users of MEG devices often must purchase magnetically shielded recording rooms costing about as much as the MEG instrument itself.

SUMMARY OF THE INVENTION

The present invention is a magnetoencephalogram (MEG) system and method which effectively removes the environmental noise from MEG recordings without manual adjustments. The system utilizes adaptive noise cancellation, which continuously and automatically adjust the weights of the reference noise channels to remove the effect of time-varying environmental sources of contamination. Another application of the present invention is the removal of other types of contaminants in MEG recordings, such as those arising from magnetic fields generated by muscle artifact, such as movement of the eyeballs.

OBJECTIVES AND FEATURES OF THE INVENTION

It is an objective of the present invention to provide a low noise magnetoencephalogram (MEG) system and method which sufficiently cancels environmental magnetic noise so that the MEG system may be utilized in a nonmagnetically shielded room.

It is a further objective of the present invention to provide such an MEG system which will automatically and rapidly compensates for changes in the magnetic environment so that the manual adjustments are not necessary.

It is a further objective of the present invention to provide such an MEG system which will not greatly add to the costs or complexity of the MEG system, but instead may utilize the existing number of channels in commercially available systems and may utilize available digital computer systems.

It is a further objective of the present invention to provide such an MEG system which will provide a set of "clean", i.e., filtered, MEG signals whose signal/-noise ratio is improved relative to alternative systems and methods.

BRIEF DESCRIPTION OF THE DRAWINGS

Other objectives of the present invention will be apparent from the following detailed description of the invention, taken in conjunction with the accompanying drawings.

In the drawings.

DETAILED DESCRIPTION

In accordance with the present invention, MEG data are treated using multidimensional adaptive noise cancellation methods. Although most adaptive filter literature has discussed noise cancellation in other contexts, from a single time series, the present invention generalizes to the multichannel case. In the present multidimensional adaptive filter, noise contributions to each MEG brain signal channel are estimated with a linear combination of past and present sample values from each of the MEG noise reference channels.

The problem is formulated as the least squares identification of the multidimensional transfer function between the noise pickup at the MEG noise reference channels and the noise pickup at the MEG brain signal channels. In this method, covariance between the MEG noise reference channels and the MEG brain signal (plus noise) channels is used to optimally (in the least squares sense) estimate and remove the noise component from the brain signal channels. A block computation uses a frame of data to form a matrix for the least squares solution. This is solved using the Householder transformation, explained below, yielding the best linear combination of noise reference channels to estimate the noise in each contaminated brain signal channel.

Given a system of prediction equations (one equation for each time point in the frame) as follows:

$$a_{10}n_1(k) + a_{11}n_1(k-1) + \ldots a_{1M}n_1(k-M) + a_{20}n_2(k) + \quad (1)$$

$$\ldots + a_{2M}n_2(k-M) + \ldots + a_{LM}n_L(k-M) = S(k) + e(k)$$

where: k is the time index; L is the number of reference channels; M is the prediction memory (i.e., how many samples into the past a current value is regressed on past reference values); $n_1(k)$ is the $k^{th}$ data value for the first noise reference channel; and $n_2(k)$ is the $k^{th}$ data value for the second noise reference channel. Or, expressed as a matrix equation $$Na - s = e \quad (2)$$

where N is the data matrix representing a system of equations in which the coefficients are the time series from the noise reference channels, a is the noise coefficient vector, i.e., the unknown weights, s is the brain signal vector, and e is the error vector.

The least squares criterion is met by that choice of a which minimizes the Euclidean length of e, written as $$\|e\| = \|Na - s\| \quad (3)$$

If Q is an orthogonal matrix, then
$$\|QNa = Qs\| = \|Na - s\| \quad (4)$$

If Q is further chosen to reduce N|s—the matrix N augmented by column vector s—to upper triangular form, the error length is minimized when a is chosen to be the solution of the transformed equations. The resulting error length is equal to the square of the lower right-hand element.

After such a computation, the noise coefficient vector (a) may be used to filter the reference noise channels to best approximate the noise in each signal channel. For the multidimensional case, each element of the coefficient vector is itself a vector, but otherwise the basic computation is the same.

In principle, the best translation between the noise reference channels and the brain signal channels is found by a calibration procedure using the above-described least squares method. However, the optimal noise reference weightings, in fact, vary significantly over the time of an MEG recording. This means that the least squares calculations must be done during the actual recordings and recalculated frequently, preferably every 0.25 seconds. Further, since the actual signal-to-noise ratio (SNR) in MEG recordings is both frequency dependent and unknown, and since the nature of the measured noise is also unknown in each frequency band (i.e., how much is independent instrumental noise, how much is dependent instrumental noise, how much is correlated with the reference channels, etc.), consecutive passes through the data over discrete frequency bands give the best overall noise cancellation.

Figure 4:
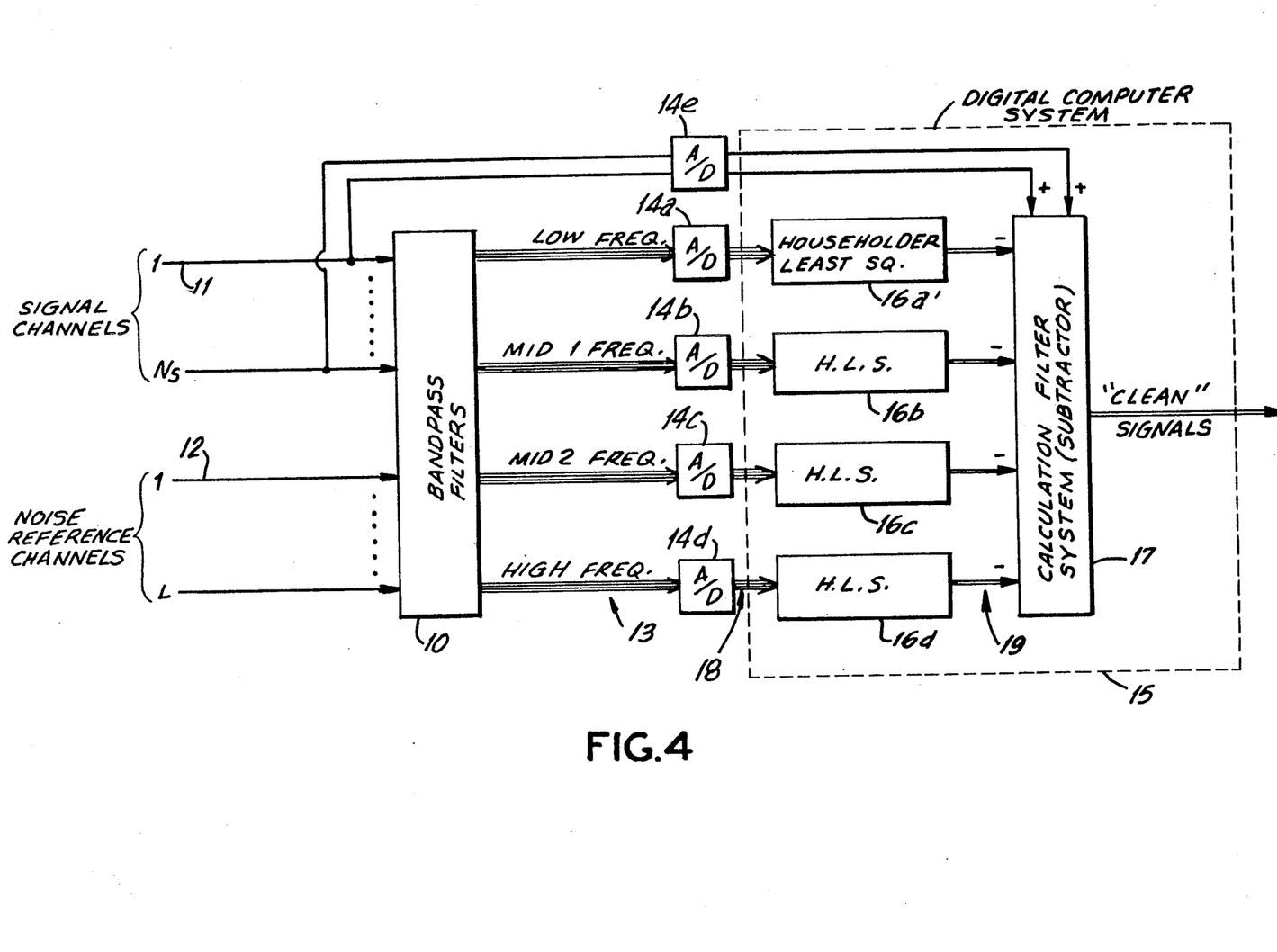
FIG. 4 is a schematic block diagram of the MEG system of the present invention. Channel lines 13 and 18 denote $N_s+L$ channels and channel lines 19 denote $N_s$ channels.

The basic steps, in sequence, of the noise reduction method, as illustrated in FIG. 4, are:

(1) Using the bandpass filters 10, separate the noise reference channels 12 (channels 1 through L) and signal channels 11 (channels 1 through $N_s$) into contiguous frequency bands 13, e.g., 1–16 Hz ("Low frequency"), 16–56 Hz ("Mid1 frequency"), 56–64 Hz ("Mid2 frequency"), and 64–120 Hz ("High frequency"). Filter 10 operates on both the signal and reference channels.

(2) For each signal and noise channel and for each frequency band of these channels, convert to digital data in A/D (analog to digital) converters 14a–14d. Break these data into 50% overlapped time windows. For example, assuming a 0.5 second window, the first time window would span from time 0 to time 0.5 seconds; the second time window would span from time 0.25 to 0.75 seconds, etc..

(3) Input each time window to the Householder blocks for analysis. In the computer system 15, the best least-squares translation function between the filtered noise reference channels 12 and the filtered signal channels is coupled consecutively for each time window using the multidimensional Householder blocks 16a–16d.

The Householder transformation translates the over-determined system of equations (as described in (1) where the system is "over-determined" since the total number of time analyzed, K, is greater than the number of times, M, used for modeling noise) into an equivalent equation. For example, the equation which has the smallest sum of squared errors will give the best solution. This happens to be an upper triangular matrix which is easily solved. Its solution gives the weights of the reference time series which yield the beat approximation to the signal time series.

Once the weights described above are calculated, the bandlimited noise time series will be weighted by these values and summed to yield an estimate of the signal time series. This estimate is then subtracted from the original time series, using calculation filter system 17. Essentially, this subtracts out the portion of the signal time series which is correlated with the noise time series.

The Householder Transformation Matrix is explained in Chapters 2, 3 and 10 of Lawson and Hanson, SOLVING LEAST-SQUARES PROBLEMS (Prentice-Hall 1974), incorporated by reference herein.

In general, the least squares ("LS") problem is solved based on a certain decomposition called an "orthogonal decomposition of A". A is $A = HRK^T$ where H is an mXm orthogonal matrix, R is an mXm matrix of the form $$R = \begin{bmatrix} R_{11} & 0 \\ 0 & 0 \end{bmatrix},$$

$R_{11}$ is a kXk submatrix of rank k and k is an nXn orthogonal matrix.

The Householder transformtion matrix for a non-zero vector V is $$Q = I_m - \frac{2\, u\, u^T}{u^T u}$$

where Q is an orthogonal matrix, $I_m$ is a matrix; $u = v + \sigma |v| e$; where $\sigma = +1$ if $v_1 \geq 0$ and $-1$ if $v_1 < 0$;

$$e = \begin{bmatrix} 1 \\ 0 \\ \vdots \\ 0 \end{bmatrix}$$

One suitable series of steps is as follows, where p, l, m, and w are integers; v is a vector (m-vector) if $w > 0$ then array contains m-vectors, $c_j$, j = 1, ..., w. The following steps compute vector u, number b, vector y = Qv, and if $w > 0$ the vectors $c_j = Qc_j$, where j = 1, ..., W.

| Step | Description |
|---|---|
| 1 | Set $s := \left( v_p^2 + \sum_{i=1}^{m} v_i^2 \right)^{\frac{1}{2}}$ |
| 2 | If $v_p > 0$, set $s := -s$ |
| 3 | Set $h := v_p - s$, $v_p := s$. |
| 4 | Comment: The construction of the transformation is complete. At Step 5 the application of the transformation to the vectors $c_j$ begins. |
| 5 | Set $b := v_p h$. |
| 6 | If $b = 0$ or $W = 0$, go to Step 11 |
| 7 | for j := 1, ..., w, do Steps 8–10 |
| 8 | Set $s := \left( c_p j h + \sum_{i=1}^{m} c_{ij} v_i \right) / b$ |

-continued

| Step | Description |
| --- | --- |
| 9 | Set $c_{pj} = c_{pj} + sh$. |
| 10 | For i: 1, ..., m, set $c_{ij} = c_{ij} + sV_i$ |
| 11 | completed. |

The above algorithm is used to reduce the N matrix augmented by the column vector s of the matrix equation $Na - s = e$. The subroutine H12 given in Appendix C of the Lawson text implements the steps 1-11 above on a digital computer using the FORTRAN programming language.

The output of the Householder block is the best estimate of the bandlimited noise component in the original signal.

(4) The bandlimited noise estimates are then passed to the Calculation Filter System block where they are summed to produce full spectrum estimates for the noise in each signal channel. Full spectrum noise estimates for each signal channel for the first half of each time window are then subtracted from corresponding time windows of digitized data from each of the signal channels. For example, using the 0.5 second window example above, the initial window of "clean" signal produced would span times 0 to 0.25 seconds, the second would span times 0.25 to 0.5 seconds, etc.

Figure 1:
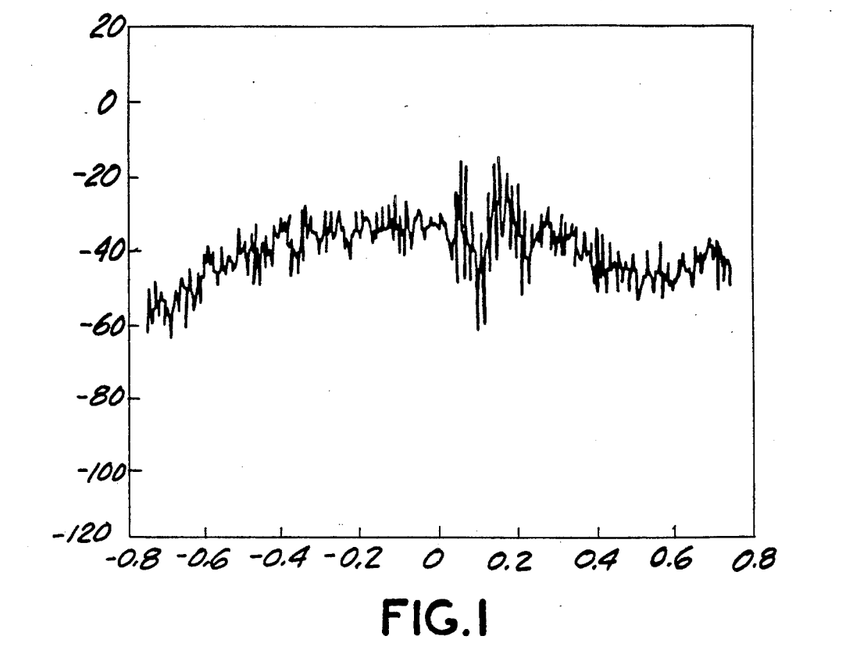
FIG. 1 is a graph of one MEG brain signal channel of the prior art showing the presence of environmental noise.
Figure 2:
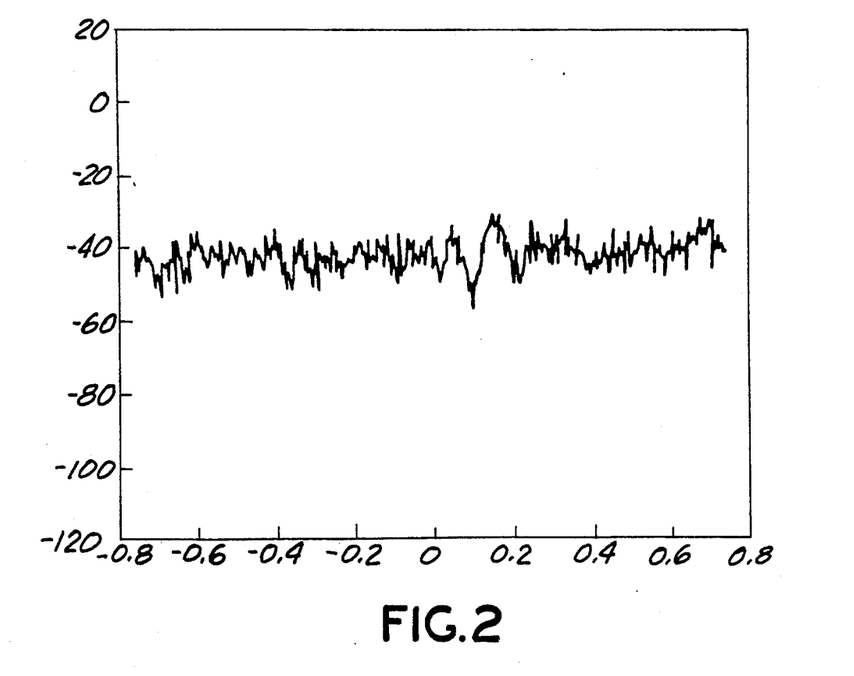
FIG. 2 is a graph of one MEG brain signal channel illustrating the effect of the filter system and method of the present invention, the signal channel being connected to a detector in the presence of a subject.
Figure 3:
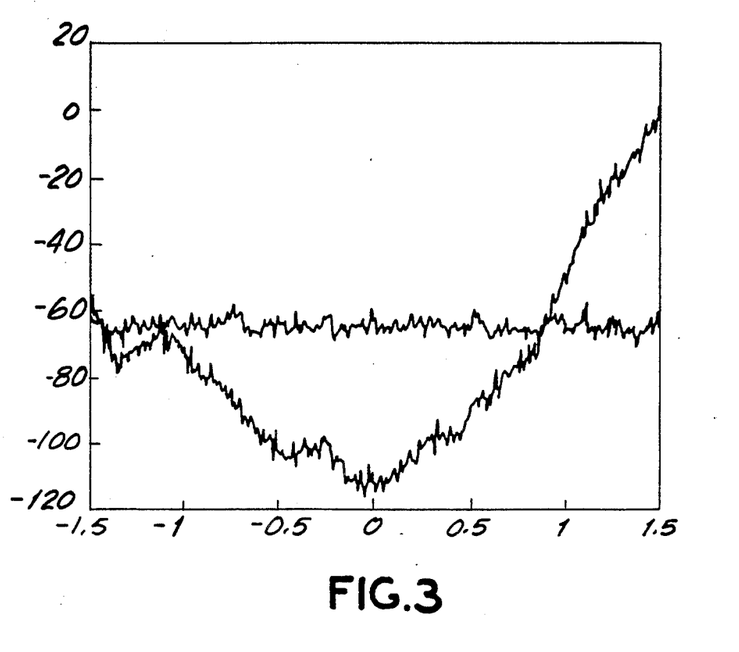
FIG. 3 is a graph similar to the graph of FIG. 2, but not related to a subject.

Evidence of the efficacy of the filter is shown in FIGS. 1, 2 and 3. These are, respectively, samples of auditory evoked (EP) magnetic field and ambient magnetic field data. The EP data consist of 5 brain signal channels connected to 5 SQUID brain signal sensor means and 4 noise reference channels connected to 4 SQUID environmental magnetic activity sensor means, 100 recordings are taken each of 2-second long trials from a healthy, right-handed adult male subject hearing a 500 msec auditory tone burst beginning 1.024 seconds into each trial, with the dewar positioned over the right temporal lobe to span both the maxima and minima of the evoked field. The data was sampled at 250 HZ and the data was averaged. Prior to analysis, the 9 channels of data were lowpass filtered at 100 HZ, highpass filtered at 0.2 HZ (48 dB/octave at each corner frequency), and filtered every 4 milliseconds. Consequently, components below 0.2 HZ and above 100 HZ were removed. Also prior to analysis, the current standard analog noise cancellation was performed after manual adjustments were made to subtract out noise; line-locked comb filtering was also performed to reduce components at 60 HZ and its harmonics.

In FIGS. 1-3, on the X-axis, 0.2=200 msec poststimulus. The Y-axis is in arbitrary units proportional to femtotesla where 1 femtotesla = $10^{-15}$ tesla. Each figure shows one channel of a 5-channel MEG recording. FIG. 1 is with averaging; but without the noise reduction system and method of the present invention. FIGS. 2 and 3 show the dramatic improvement in one MEG channel resulting from application of the filtering method and system of the present invention. The improved evoked MEG field response was obtained from the average of 100 trials that had been noise-filtered using 0.5 second windows with a 50% overlap, and 4 consecutive noise removal steps over differing (0-16, 16-56, 56-64, 64-128 HZ) frequency bands. Remanent line-related noise was removed in an effectively perfect notch without any hand-tuning or special notch filters. Low frequency noise was also removed.

As seen in FIG. 2, the filtering of the present invention eliminates most of the low- and high-frequency noise. The evoked brain magnetic field peak at approximately 95 msec is quite evident.

FIG. 3 shows the average of 50 segments of MEG recorded with the same apparatus but without a human subject. The noise removal has subtracted almost all of the noise. The remanent is likely due to the intrinsic residual noise of the SQUID detectors themselves, and not noise from external contaminants.

FIG. 3 shows the average MEG waveforms for 50 epochs of 3 seconds, without a human subject in the apparatus. Prior to filtering, the data were analog filtered to remove components below 0.2 HZ and above 50 HZ using 48 dB/octave filters. Sampling was at 125 HZ. FIG. 3 shows the original waveform from one channel of a 5-channel MEG recording along with the same waveform after noise filtering. The filtering used 0.5 second analysis windows with 50% overlap and four separate frequency bands. The separation into frequency bands tend to separate out the different sources of noise which have different optimal reduction solutions. This is due to the facts that simple least square methods will be dominated by the largest frequency component and the sources of noise will tend to have both radically different spectra and direction of original.

Since the frequency bandsplitting is a significant fraction of the computation, the embodiment shown in FIG. 4 includes digitization of the outputs of analog bandpass filters as well as the wideband channels. In another embodiment, shown in FIG. 5, special-purpose dedicated digital hardware, including digital bandpass filter 10A, is used to perform the noise cancellation. In a third embodiment, shown in FIG. 6, software filters have been designed to work within the constraints of a general-purpose laboratory computing environment.

Figure 5:
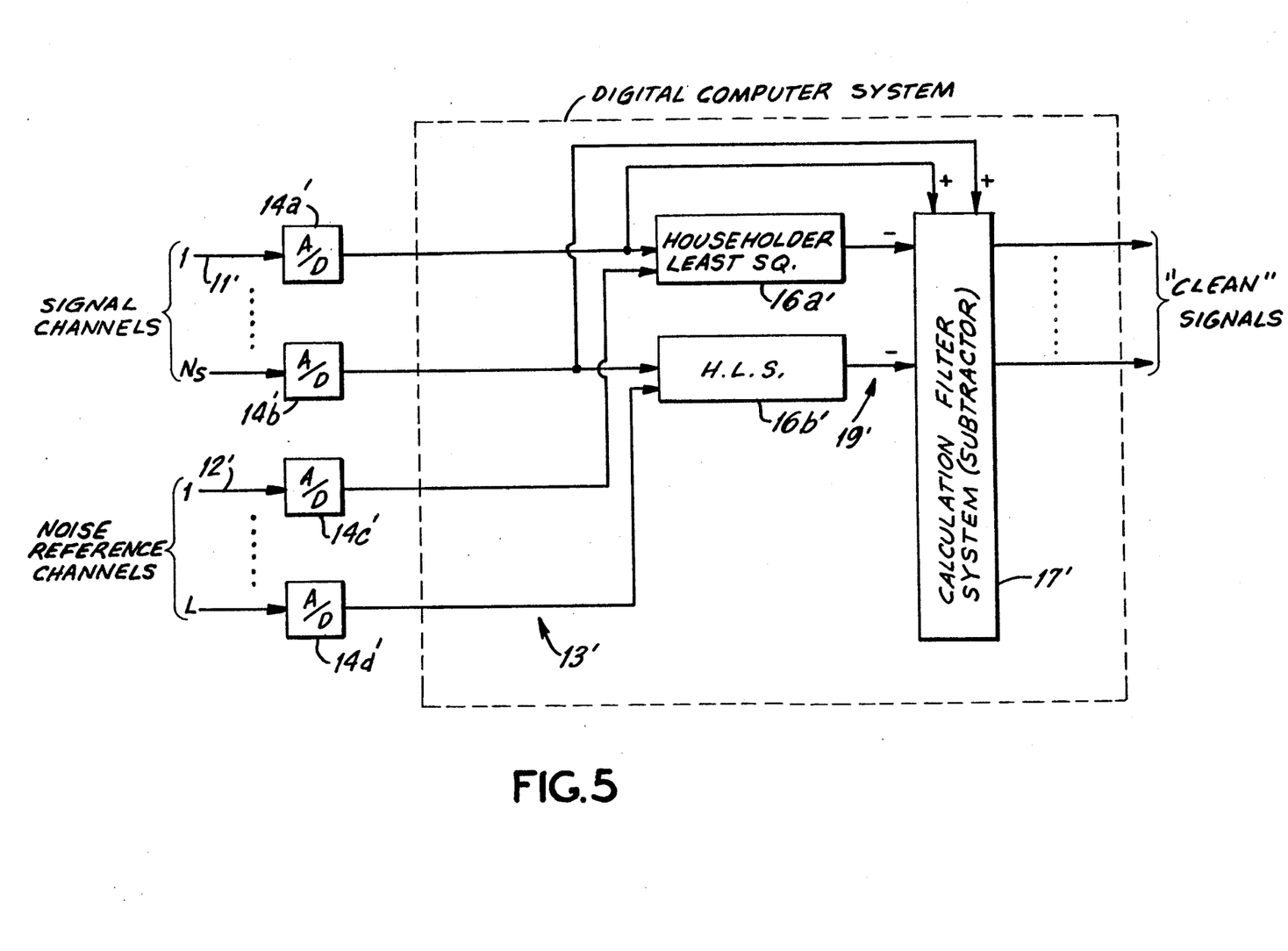
FIG. 5 is a schematic block diagram of another embodiment of the MEG system of the present invention illustrating the case where noise reduction is not separately applied to frequency bands but is applied to full spectrum signals.
Figure 6:
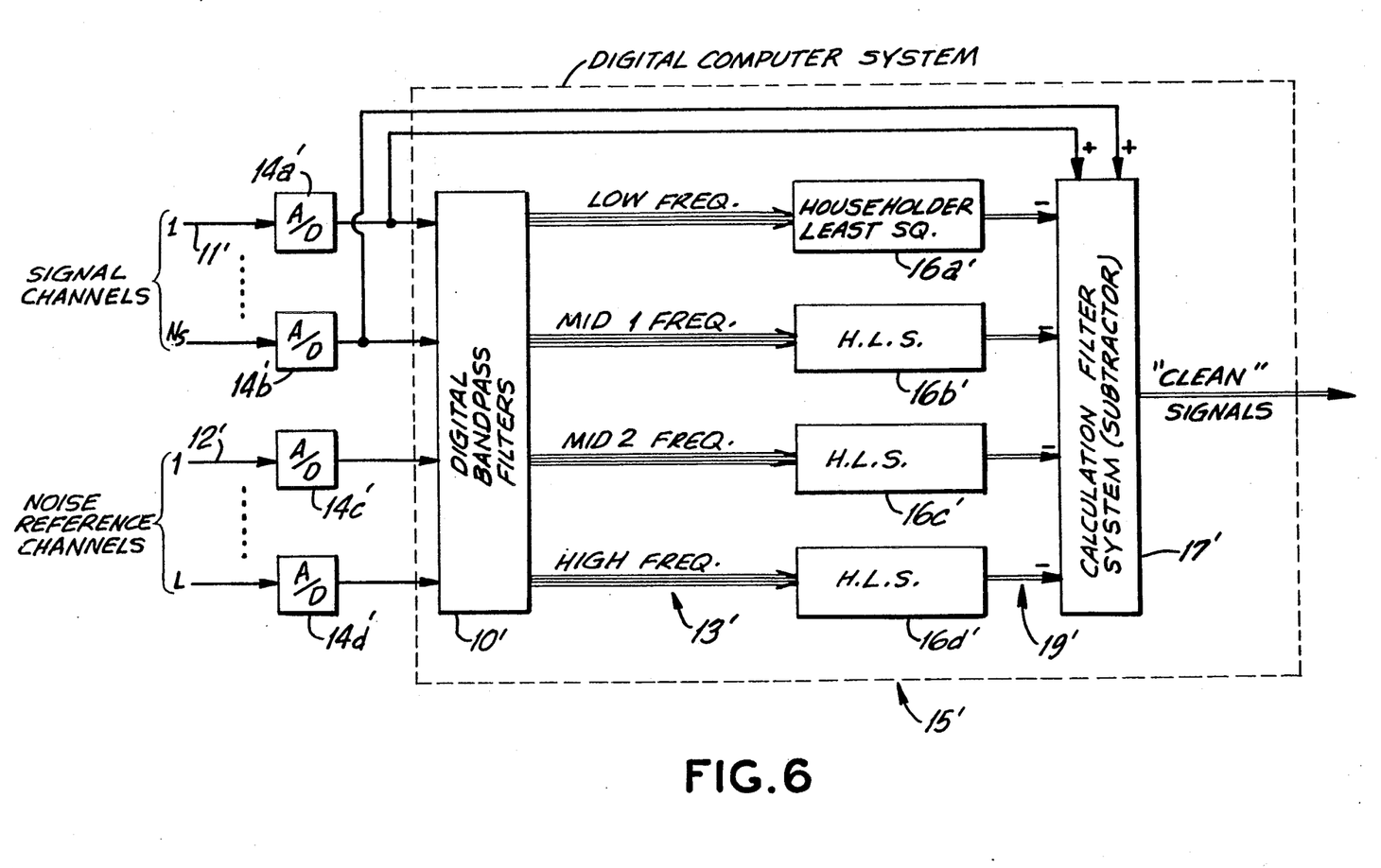
FIG. 6 is a schematic diagram of yet another embodiment of the MEG system of the present invention illustrating the case where digital bandpass filters are used instead of analog filters. Channel lines 13' denote $N_s+L$ channels; channel lines 19' denote $N_s$ channels.

In FIGS. 4, 5, and 6 the signal channels 11, 11', and 11", respectively, are channels 1 through $N_S$; the environmental noise channels 12, 12', and 12", respectively are channels 1 through L. In FIG. 4, the channels 11 and 12 are connected to bandpass filters 10 whose outputs, on four multi-channel lines 13 (low freq, med 1 freq, and 2 freq, high freq) are to respective analogue-digital converters (A/D) 14a-14d. Each A/D 14a-14d is connected to a Householder least square means 16a-16d in digital computer system 15, and each of the four least square means 16a-16d is connected to calculation filter system (subtractor) 17, to which A/D 14e is also connected. In FIG. 5 the A/Ds 14a', 14b' are connected to HLS (Householder Least Squares) 16a', 16b', respectively and A/Ds 14c', 14d' are connected to HLS 16a', 16b', respectively on digital computer system 15', which also includes calculation filter system (subtractor) 17'.

Figure 7:
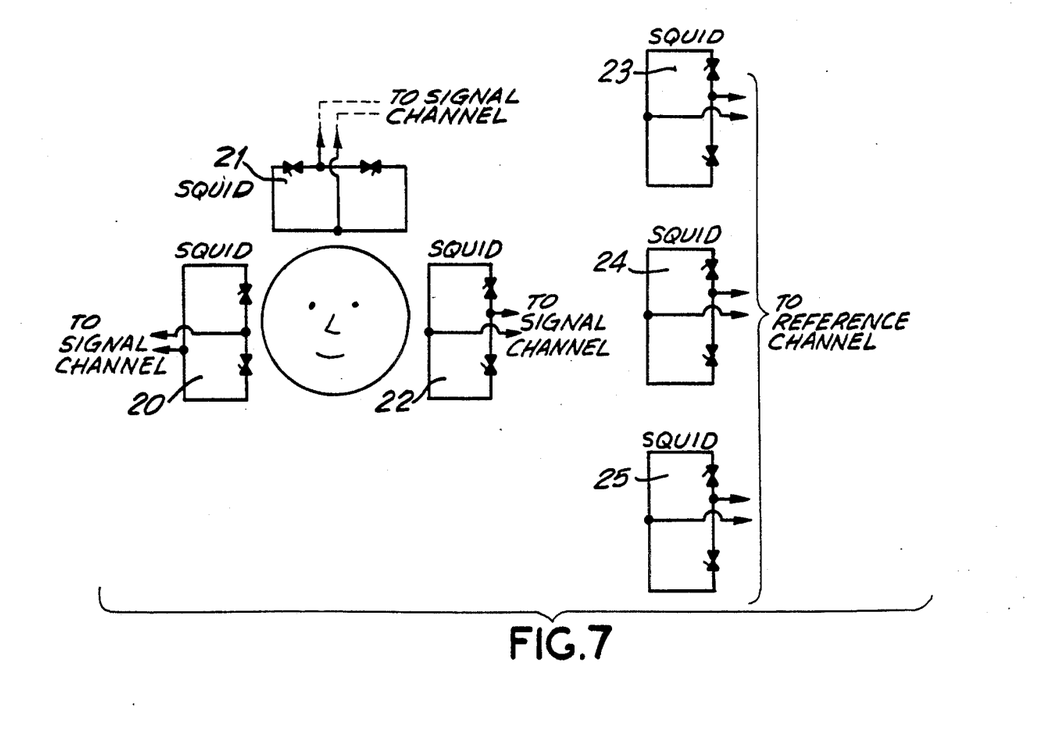
FIG. 7 is a diagram schematizing the signal recording situation referenced by the present invention description. Three SQUIDs are shown placed about a subject's head; these are the "signal" channels. Three other SQUIDs are shown place remote from the subject's head; these are the "reference" channels.

In the embodiment of FIG. 7 three SQUIDS 20-22 are connected to brain signal channels (channels 11 of FIG. 4) and three SQUIDS 23-25 are connected to environmental noise reference channels (channels 12 of FIG. 4).

Preferably the system uses one to fourteen magnetic sensor means adjacent the head of the subject to detect neuromagnetic brain signals and three to eight magnetic sensor means to detect the environment.

What is claimed is:

1. A low noise magnetoencephalogram (MEG) system in an environment having magnetic activity, the system being for the detection of brain neuromagnetic activity of a human subject, including:

a first plurality of magnetic sensor means at least part of each sensor means being adapted to be positioned adjacent the head of a subject to detect neuromagnetic brain signals; a plurality of brain signal channels, each brain signal channel connected to one of said first magnetic sensor means;

a second plurality of magnetic sensor means to detect signals from environmental magnetic activity; a plurality of environmental noise reference channels, each reference channel being connected to one of said second magnetic sensor means;

a bandpass filter means, connected to the brain signal channels and the reference channels to separate said brain signals and environmental signals into a plurality of predetermined frequency bands and reject said signals not within said predetermined frequency bands;

computer transformation means which act separately on each of said frequency bands to provide a least squares noise component estimate of the noise component present in each brain signal channel;

computer calculation means to algebraically subtract said least square noise component estimate from the signals in each brain wave channel thereby providing a filtered brain signal having reduced noise.

2. A magnetoencephalogram (MEG) system as in claim 1 wherein the transformation means uses a Householder transformation matrix to provide the least square estimate.

3. A magnetoencephalogram (MEG) system as in claim 1 the system comprises at least 5 brain signal channels and 4 reference channels.

4. A magnetoencephalogram (MEG) system as in claim 1 wherein said bandpass filter means include at least 4 bandpass filters.

5. A magnetoencephalogram (MEG) system as in claim 1 wherein each of the sensor means is a SQUID (superconducting quantum interference device).

6. A noise reduction method in a magnetoencephalogram (MEG) for the detection of human brain neuromagnetic activity of a subject in an environment having noise magnetic activity including:

positioning a plurality of magnetic sensor means adjacent to the head of a subject to detect neuromagnetic brain signals; connecting a brain signal channel to each of said brain signal magnetic sensor means;

positioning a plurality of magnetic sensor means to detect the environmental magnetic activity; connecting a reference channel to each of the environmental magnetic senor means;

separating the signals from each of the channels into a plurality of frequency bands using a bandpass filter means connected to the brain signal channels and the reference channels;

automatically providing a least squares estimate of the noise component present in each brain signal channel and applying said least squares estimate to each of said frequency bands;

automatically algebraically subtracting said noise component estimate from the signals in each brain wave channel thereby providing a filtered brain signal having reduced noise.

7. A noise reduction method as in claim 6 wherein 3 brain signal channels are connected to 3 brain signal magnetic sensor means and 3 reference channels are connected to 3 environment magnetic sensor means.

8. A noise reduction method as in claim 6 and using a Householder transformation matrix to provide the least squares estimate.

9. A noise reduction method as in claim 6 wherein the frequencies within the bandpass range are divided into at least 4 frequency bands.

10. A noise reduction method as in claim 6 and including the step of locating the sensor means in a non-magnetically shielded room.

* * * * *